(12) United States Patent
Nakajima et al.

(10) Patent No.: US 6,313,167 B1
(45) Date of Patent: Nov. 6, 2001

(54) COMPOSITION HAVING CAPABILITY OF REMOVING RISK FACTOR DURING EXERCISE

(75) Inventors: Shuji Nakajima; Tetsuya Murakami; Yoichi Sekiguchi, all of Tokyo (JP)

(73) Assignee: Nippon Suisan Kaisha Ltd., Tokyo (JP)

( * ) Notice: Subject to any disclaimer, the term of this patent is extended or adjusted under 35 U.S.C. 154(b) by 0 days.

(21) Appl. No.: 09/445,807

(22) PCT Filed: Jun. 15, 1998

(86) PCT No.: PCT/JP98/02616
§ 371 Date: Apr. 27, 2000
§ 102(e) Date: Apr. 27, 2000

(87) PCT Pub. No.: WO98/57628
PCT Pub. Date: Dec. 23, 1998

(30) Foreign Application Priority Data

Jun. 16, 1997 (JP) .................................................. 9-158218
Dec. 27, 1997 (JP) .................................................. 9-367978
Dec. 27, 1997 (JP) .................................................. 9-367979

(51) Int. Cl.$^7$ ........................ A61K 31/22; A61K 31/225; A61K 31/20
(52) U.S. Cl. ........................ 514/546; 514/547; 514/558; 514/560
(58) Field of Search ........................ 514/546, 547, 514/558, 560

(56) References Cited

U.S. PATENT DOCUMENTS 5,587,190  12/1996  Guezennec et al. ..................... 426/2

FOREIGN PATENT DOCUMENTS

| 2 221 843 A | 8/1989 | (GB) . |
| 57-047446 | 3/1982 | (JP) . |
| 57-086254 | 5/1982 | (JP) . |
| 59-210870 | 11/1984 | (JP) . |
| WO 87/03899 | 7/1987 | (WO) . |

OTHER PUBLICATIONS

Akira Ito et al., "Studies on the Sports Anemia", Bull. Health & Sports Sciences. Univ. of Tsukuba 9: 181–193 (1986).

Sawaki Keisuke et al., "The Effect on Long Distance Runners by Long Term Taking Omega–3 Fatty Acid", Clinical Report vol. 30, No. 11: 3097–3101 (1996).

*Primary Examiner*—Kevin E. Weddington
(74) *Attorney, Agent, or Firm*—Armstrong, Westerman, Hattori, McLeland & Naughton, LLP

(57) ABSTRACT

The composition of the invention contains an n-3 highly unsaturated fatty acid as the active ingredient and has the capability of removing a risk factor during exercise, particularly the capability of preventing athletic anemia. The highly unsaturated fatty acids and/or derivatives thereof, preferably eicosapentaenoic acid and/or docosahexaenoic acid. It is most preferably in the form of a natural triglyceride, particularly a fish oil. The composition may be used as a medicament or a food composition, particularly a food for sports. In the case of the medicament, the composition derivative is a pharmaceutically acceptable salt, ester, or amide. The capability of removing a risk factor refers to the capabilities of improving the maximum oxygen intake and increasing the anaerobic threshold value by at least 3%. In this case, the composition serves as a food for enhancing the exercise capacity of persons with a normal healthy body.

29 Claims, 11 Drawing Sheets

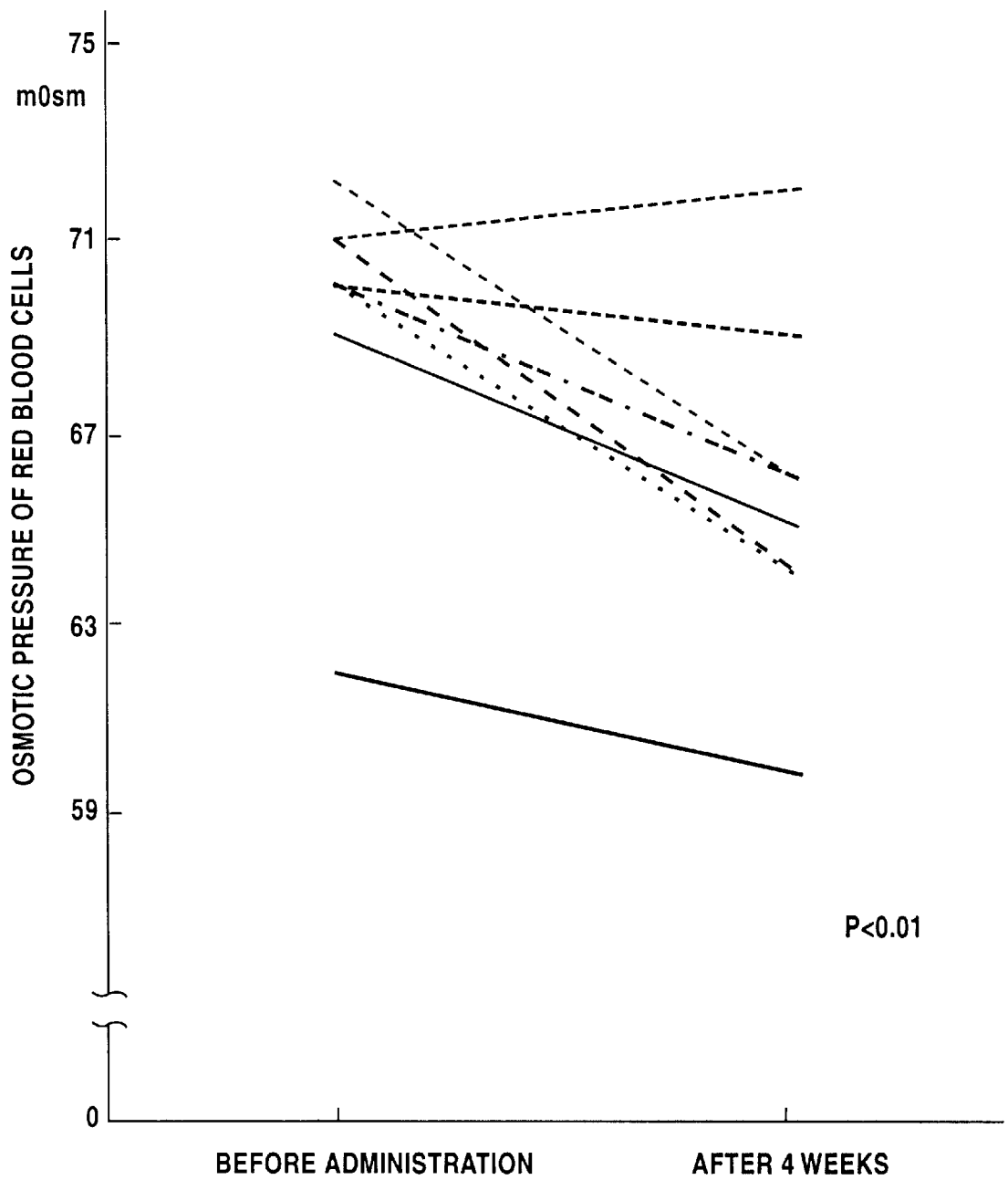

COMPOSITION HAVING CAPABILITY OF REMOVING RISK FACTOR DURING EXERCISE

FIELD OF THE INVENTION

This invention relates to a composition having a capability of removing a risk factor during exercise, which can be utilized in the field of foods, prophylaxis, and medical care. This invention also relates to a food for persons with a normal healthy body, such as sport enthusiasts, persons who want to do sports, and persons who aim to improve stamina. In addition this invention relates to a nutritious food for improving exercise capacity, which can enhance the aerobic capacity and is effective as auxiliary means for improving the athletic capability in long-distance running.

BACKGROUND OF THE INVENTION

People are encouraged to do exercise because exercise may make metabolism proceed smoothly to remove a risk factor for adult diseases. A considerable number of medical reports have been published on the effect of exercise as a means for rehabilitation of patients of myocardial infarction. On the other hand, various diseases and complications resulted from doing sports are problems in sports medicine, including 'athletic anemia' and 'sudden death'.

Causes of athletic anemia may include insufficient red blood cell production due to accelerated protein metabolism during exercise and/or insufficient iron intake, hemolysis by chemical substances such as lactic acid produced during exercise, and hemolysis by physical actions such as impulse during exercise.

Many of the cases of sudden death have chronic underlying diseases, though some of the cases seem morphologically to have no underlying disease where definite diagnosis is often very difficult. Many cases of sudden death during sports have been reported; sudden death occurs most frequently during running sports such as running, jogging, and marathon, and frequently during playing basketball, baseball, and swimming.

Cases of sudden death may be classified into two groups; one group with latent organic underlying diseases, and one group with mild organic underlying diseases or without remarkable organic change. Cases of the former group rarely become problematic because they have subjective symptoms and some of them are under medical treatment. However cases of the latter group may become problematic and may frequently give rise to public discussion because they have no subjective symptoms, are judged to have no abnormality in medical examination, but die suddenly as a result of action such as doing sports. Cases of acute heart failure of unknown cause in the young (so-called a disease causing sudden death) belong to the latter group, and frequently give rise to public discussion in relation with the excessive exercise or rigorous training.

The nature of acute heart failure in the young still remains unknown and there are various views on the nature. Generally a seemingly healthy and robust young man (Acute heart failure occurs mostly in men.) falls down abruptly with a groan to die suddenly. Autopsy of such a man reveals mild cardiac hypertrophy accompanying enlargement of the heart, thinning and narrowing of vessels including coronary artery and aorta, and other findings, though arteriosclerosis is rarely found. The possibility that sudden death may follow arrythmia during or after exercise should be taken into account.

It has been clarified that EPA and DHA have physiological actions including decrease of neutral lipid and total cholesterol in blood, increase of HDL cholesterol, reduction of platelet aggregation, reduction of blood viscosity, and elevation of fragility of red blood cells. These actions make blood flow fluently and aggregate with difficulty. DHA, being rich in the tissue of the brain cell membrane, has been expected to have some influence on the function related to the nerve tissue, such as learning function, and is being studied actively.

Sawaki et al.(Juntendo University) noticed that the Norwegian athletes who obtained good results in the Lillehammer Winter Olympic Game had taken DHA and EPA as auxiliary nutritious foods, and studied the influence of intake of DHA and EPA on the training effect in the track and field athletes. The study showed that there is a great difference between those who took DHA/EPA and those who did not, and it was assumed that intake of DHA/EPA may enhance the oxygen-transporting ability to capillaries.

Studies on the influence of such fatty acids on exercise capacity will be made more actively in future, and development of practical techniques supported by the results of studies is awaited. The relationship between the reduced fragility of red blood cells and hardened membrane of red blood cells has been reported in several diseases, and increased fluidity of the red blood cell membrane may make red blood cells fragile. Based on these findings, agents to remove risk factors during exercise are being expected to be developed in the field of prophylaxis and medical care.

DISCLOSURE OF THE INVENTION

The purpose of this invention is to provide a health food for preventing athletic anemia, a health food for preventing risks during exercise such as sudden death, and a composition capable of removing a risk factor during exercise which can be utilized in the field of preventive pharmaceuticals. Another purpose of this invention is to provide a composition capable of removing a risk factor during exercise for healthy persons, such as professionals of sports, sport players or athletes, sport enthusiasts, persons who want to do sports, and persons who aim to improve stamina, in the form of a food for sports or a pharmaceutical composition.

An additional purpose of this invention is to provide a food which can improve exercise capacity for healthy persons such as sports enthusiasts, persons who want to do sports, and persons who aim to improve stamina. A further additional purpose of this invention is to provide a nutritious food for improving exercise capacity which can enhance the aerobic capacity and is effective as auxiliary means for improving the athletic capability in long-distance running.

It has been proposed that the change in blood rheology during exercise may be a cause of sudden death.

The inventors built up a working hypothesis "seafood may improve the blood viscosity", and conducted an epidemiological study in fishermen with much intake of fish meat and farmers whose fish meat intake is less than that of fishermen, and fundamental and clinical studies of fish oil concentrates and highly purified eicosapentaenoic acid ethyl ester (EPA.EE). The inventors found already that EPA, an ingredient of fish oil, can improve blood viscosity.

Since then the inventors have studied the action mechanism of EPA in red blood cell membrane from the hemorheological viewpoint.

The inventors first found that an n-3 highly unsaturated fatty acid not only influences hemorheology under normal conditions but also suppresses undesirable changes in hemorheology due to exercise, making it possible to provide a health food and a preventive pharmaceutical for preventing risks during exercise such as sudden death.

The gist of this invention is a composition capable of removing a risk factor during exercise characterized in that it contains an n-3 highly unsaturated fatty acid as an active ingredient. Said capability of removing a risk factor is the capability of preventing athletic anemia, and therefore the gist of this invention is a composition having capability of preventing athletic anemia characterized in that it contains an n-3 highly unsaturated fatty acid as an active ingredient. Said n-3 highly unsaturated fatty acid is an n-3 highly The result of the measurement is shown in Table 1.

The maximum oxygen intake is 70.7±4.1 ml/kg/min on the average. The limit for a man is said to be 83 to 85 ml/kg/min. If the response to training on the flatland or to some treatment is a change by 3 to 5%, the response is considered to be significant in the subjects who have higher values than normal persons.

TABLE 1

| Name | Height cm | Body weight kg | Exercise duration | Maximum voluntary ventilatio l/min | Maximum oxygen intake ml/kg/min | | Maximum heart rate beat/min | Maximum respiration rate ml/l | Respiration efficiency ml/l | Tidal volume ml | Respiratory exchange ratio |
|---|---|---|---|---|---|---|---|---|---|---|---|
| Y. Y | 168.0 | 56.8 | 18 min 06 sec | 125.8 | 4.044 | 71.2 | 182 | 56.0 | 32.1 | 2248 | 1.16 |
| T. K | 184.0 | 67.8 | 17 14 | 159.3 | 4.503 | 66.4 | 180 | 64.0 | 28.3 | 2489 | 1.04 |
| T. O | 165.0 | 47.3 | 16 52 | 115.4 | 3.375 | 71.4 | 191 | 66.0 | 29.2 | 1750 | 1.08 |
| Y. N | 176.0 | 60.2 | 17 42 | 124.7 | 3.692 | 61.3 | 200 | 65.0 | 29.6 | 1890 | 1.09 |
| T. M | 177.0 | 57.7 | 18 08 | 157.3 | 4.275 | 74.1 | 205 | 68.0 | 27.2 | 2314 | 1.07 |
| K. K | 168.0 | 57.3 | 17 21 | 151.9 | 4.179 | 72.9 | 194 | 94.0 | 27.5 | 1617 | 1.07 |
| S. O | 169.0 | 55.4 | 17 46 | 147.8 | 4.183 | 75.5 | 198 | 96.0 | 28.3 | 1541 | 1.05 |
| M. K | 181.0 | 71.8 | 17 13 | 157.8 | 4.887 | 68.1 | 173 | 68.0 | 31.0 | 2322 | 1.03 |
| N. S | 166.0 | 53.2 | 18 40 | 126.9 | 3.640 | 68.4 | 196 | 68.0 | 28.7 | 1867 | 1.08 |
| H. S | 173.0 | 59.5 | 17 40 | 153.9 | 4.485 | 75.4 | 202 | 65.0 | 29.1 | 2332 | 1.03 |
| S. M | 166.0 | 51.9 | 18 16 | 120.9 | 3.648 | 70.3 | 196 | 90.0 | 30.2 | 1344 | 1.06 |
| K. T | 176.0 | 55.2 | 18 19 | 130.2 | 4.508 | 72.1 | 200 | 64.0 | 30.5 | 2036 | 1.13 |
| T. H | 173.0 | 65.2 | 18 21 | 159.5 | 4.736 | 72.6 | 191 | 73.0 | 29.7 | 2194 | 1.06 |
| M. F | 172.0 | 53.8 | 17 52 | 138.5 | 3.874 | 72.0 | 200 | 76.0 | 28.0 | 1823 | 1.09 |
| T. S | 167.0 | 53.4 | 18 23 | 162.3 | 4.051 | 75.9 | 209 | 98.0 | 25.0 | 1657 | 1.08 |
| M. S | 180.0 | 63.5 | 17 38 | 154.7 | 4.517 | 71.1 | 209 | 72.0 | 29.2 | 2149 | 1.13 |
| T. T | 179.0 | 59.9 | 17 14 | 132.7 | 3.780 | 63.1 | 202 | 62.0 | 28.5 | 2141 | 1.15 | unsaturated fatty acid and/or a derivative thereof. Said n-3 highly unsaturated fatty acid is eicosapentaenoic acid and/or docosahexaenoic acid. Said n-3 highly unsaturated fatty acid is preferably in the form of a natural triglyceride such as that in fish oil. The composition of this invention having the capability of removing a risk factor during exercise is suitable for a food composition, particularly a food for sports. The composition of this invention can be used also as a pharmaceutical composition, where the derivative of n-3 highly unsaturated fatty acid is a pharmaceutically acceptable salt, ester, or amide.

The inventors have tried oral administration of vitamin E, vitamin C, or squalene (the main component of liver oil of deep-sea shark) as an supplementary means for improving stamina. The inventors found from the results of the exercise capacity test within the laboratory and biochemical experiments that vitamins E and C act synergistically to be effective in improving exercise capacity and that squalene is also effective in enhancing aerobic capacity of trained long-distance runners. Based on these findings, this invention focused on the n-3 highly unsaturated fatty acids as a food which has been demonstrated to enhance oxygen supply in the microcirculation and be effective in improving the aerobic capacity. There is few scientific proof for effectiveness of the n-3 highly unsaturated fatty acids contained in fish oil, with few case studies in long-distance runners having high athletic capability.

The maximum oxygen intake means the amount of oxygen that a person can take up into the body during exercise that can be continued for about 5 minutes with the greatest efforts, and the higher the maximum oxygen intake, the more desirable for the person. The maximum oxygen intake was measured in 17 persons including those other than the subjects.

Said capability of removing risk factors is a function to enhance the maximum oxygen intake and the anaerobic threshold value by at least 3%, and therefore the gist of this invention is a composition having a function of enhancing the maximum oxygen intake and the anaerobic threshold value by at least 3% characterized in that the composition contains an n-3 highly unsaturated fatty acid as the active ingredient.

Said food is a food capable of improving exercise capacity of healthy persons, and therefore the gist of this invention is a food capable of improving exercise capacity of healthy persons characterized in that the food has a function of enhancing the maximum oxygen intake and the anaerobic threshold value by at least 3%.

In more concrete, the gist of this invention is a food capable of improving exercise capacity of healthy persons characterized in that it contains eicosapentaenoic acid and/or docosahexaenoic acid and has a function of enhancing the maximum oxygen intake and the anaerobic threshold value by at least 3%.

Said food is a liquid or solid. Said food may be in the form of capsules.

In this invention, the n-3 highly unsaturated fatty acid used is an n-3 highly unsaturated fatty acid and/or a derivative thereof. For a composition for foods, a free fatty acid and/or a glyceride ester is used, and for a pharmaceutical composition, a free fatty acid, and a pharmaceutically acceptable salt, ester, or amide thereof is used.

In more concrete, fat and oil compositions with n-3 highly unsaturated fatty acids as the major ingredient, such as refined fish oil, refined fish oil enriched in eicosapentaenoic acid and/or docosahexaenoic acid, and fat and oil compositions with higher absorption in which n-3 highly unsaturated fatty acids account for more than 60% of the constituting fatty acids with medium chain fatty acids accounting for the remaining portion; and fatty acids or a mixture of esters thereof obtained from natural fat and oil rich in eicosapentaenoic acid or derivatives thereof such as glycerides may be used. For example fatty acids or mixtures of esters obtained from fish selected suitably among sardine, mackerel, herring, pacific saury, etc., and animal marine plankton selected suitably among krill and the various shrimp-like copepodes known in Japanese as "okiami" may be used.

Said refined fish oil are obtained by refinement of sardine oil, tuna oil, pacific saury oil, herring oil, mackerel oil, cod liver oil, squid oil, menhaden oil, etc. by alkali refining, bleaching, deodorization, degumming, wintering, etc. Such refined fish oil is exemplified by the refined fish oil with a total amount of EPA and DHA of 20 weight % or more, and tasteless and odorless fish oil with 0.1% or less of cholesterol and a high content of EPA/DHA.

Refinement of fish oil is performed for removal of free fatty acids, odor components, coloring components, etc. from crude oil collected from the raw material. Methods of refinement includes refinement with alkali, steam blowing, adsorption, etc., which may be combined as needed. Refinement with alkali is called also deoxygenation, where free fatty acids in fish oil are converted into foots by addition of sodium hydroxide to crude oil, impurities are adsorbed to or dissolved in the foots, and the resultant foots are removed. Steam blowing refinement is a method where refined oil is heated to around 150° C. under reduced pressure, into which steam is blown to remove odor components. Refinement by adsorption is a method where coloring components and odor components in crude oil are adsorbed and removed by using an adsorbent such as activated carbon and acid clay.

Fish oil is refined until it becomes tasteless and odorless by utilizing these publicly known methods, and then cholesterol is removed practically completely from fish oil. In the Examples of this invention fish oil is used after refinement to tasteless and odorless oil with 0.1% or less of cholesterol and high content of EPA/DHA. Fatty acids such as EPA and DHA contained in tasteless and odorless fish oil used in the Examples of this invention are present in the form of triglycerides. The content of EPA and DHA may be varied according to the purpose of use, etc.; for example, fish oil with 18% of EPA and 8 to 12% of DHA, fish oil with 28% of EPA and 12% of DHA, and fish oil with 5 to 8% of EPA and 22% of DHA. Any fish oil used contains 0.1% or less of cholesterol.

Said highly purified EPA and the ester thereof are produced as follows: a mixture of fatty acids or esters thereof obtained from natural fat and oil containing eicosapentaenoic acid and/or the derivatives thereof is subjected to precision distillation in two or more distillation towers under high vacuum, and the distillate containing C-20 fatty acids or esters thereof as the major ingredient is collected and then fractionated for purification by reversed phase column chromatography. Said highly purified DHA and the ester thereof are produced by a similar procedure.

The composition of this invention having a capability of removing risk factors during exercise is suitable for utilization in the field of health foods and preventive drugs that can prevent risks such as sudden death during exercise. Compositions having a capability of removing risk factors during exercise for healthy persons such as sports professionals, sports players or athletes, sports enthusiasts, persons who want to do sports, and persons who aim to improve stamina can be utilized as sports foods. The compositions can be used also as pharmaceutical compositions.

When the invention is used as a health food to prevent risks such as sudden death during exercise, arbitrary ingredients such as vitamins, carbohydrates, pigments, flavors, etc. may be added properly in addition to the essential ingredient n-3 highly unsaturated fatty acids. An emulsifier may be added as needed. Such emulsifiers include glycerol esters of fatty acids, sucrose esters of fatty acids, sorbitan esters of fatty acids, soybean phospholipid, and propylene glycol esters of fatty acids, which may be used separately or in combination. Foods may be eaten in an arbitrary liquid or solid form, or in the form of soft capsules prepared by enveloping foods with gelatin. Capsules are made with gelatin film prepared by dissolution of the starting gelatin in water followed by addition of a plasticizer (glycerol, D-sorbitol, etc.).

Said composition is usable as a pharmaceutical for removal of risk factors during exercise containing an n-3 highly unsaturated fatty acid or a pharmaceutically acceptable salt, ester, or amide thereof as the active ingredient. In this case said n-3 highly unsaturated fatty acid is eicosapentaenoic acid and/or docosahexaenoic acid, and not only the acids themselves but also pharmaceutically acceptable salts, esters, or amides thereof are used. For said pharmaceuticals, an n-3 highly unsaturated fatty acid may be used alone as a pharmaceutical preparation, and also as a pharmaceutical composition produced by addition of a pharmaceutically usable carrier or diluent. Such a pharmaceutical preparation or a pharmaceutical composition may be administered orally or parenterally. For example, a solid or fluid (gel and liquid) pharmaceutical preparation or composition for oral administration may be in the form of confectionary tablets, capsules, tablets, pills, powders, granules, or gel preparations. The exact dose of a pharmaceutical preparation or composition varies according to the form of use and duration of treatment, and is determined appropriately by the physician or veterinarian in charge. It is evident that a pharmaceutical preparation or composition used as a drug for removing risk factors during exercise containing an n-3 highly unsaturated fatty acid as the active ingredient may be used in combination with treatment with another pharmaceutically active substance.

Foods of this invention for improving exercise capacity of healthy persons are taken as daily nutritional supplements for improving exercise capacity of healthy persons such as sports enthusiasts, persons who want to do sports, persons who aim to improve stamina, and others. Continued intake of daily nutritional supplements will enhance aerobic capacity and improve exercise capacity of healthy persons.

Also when the invention is utilized as the foods for improving exercise capacity of healthy persons, arbitrary ingredients may be added properly as when this invention is utilized as healthy foods for preventing risks such as sudden death during exercise as described above.

There are various factors that influence blood viscosity, including red blood cell fragility, hematocrit, and plasma viscosity. These factors may give influence to each other to change viscosity. EPA is supposed to improve red blood cell fragility among these factors. Red blood cell fragility is dependent on the surface area/cubic volume ratio of red blood cells, internal viscosity of red blood cells, viscoelasticity of the membrane, etc.

After 10-day administration of refined fish oil to healthy persons, hematocrit remained unchanged both in the group given fish oil and in the group without administration of fish oil, but red blood cell fragility increased significantly in the group given fish oil, while increase of the yield value noted in the group without administration of fish oil was not observed in the group given fish oil.

BRIEF DESCRIPTION OF THE DRAWINGS

FIG. 11 illustrates the influence of 4-week administration of EPA-EE on red blood cell osmotic pressure (at the end of hemolysis) in healthy persons.

BEST EMBODIMENTS OF THE INVENTION

This invention is explained in the following concrete Examples, but this invention is not limited by these Examples at all.

EXAMPLE 1

In this Example, an n-3 fatty acid was experimentally administered to subjects for a certain period, and the influence on the performance in the race (10,000 m running race) was investigated in cooperation with the Laboratory of Measurement of Physical Fitness, Juntendo University.

In practice, the 10,000 m running records of the athletes belonging to the field and track athlete club of Juntendo University in two years were investigated for comparison. Training in the first year was equivalent both quantitatively and qualitatively to that in the next year and was performed under the same environmental conditions according to the annual training schedule. The 10,000 m running records used were those collected at almost the same time of the year for the two years. In the first year 1994, n-3 fatty acid was not given, whereas in the next year 1995 six capsules containing n-3 fatty acid were given regularly every day, 3 in the morning and 3 in the evening, and the influence of administration of n-3 fatty acid on the record was investigated.

Figure 1:
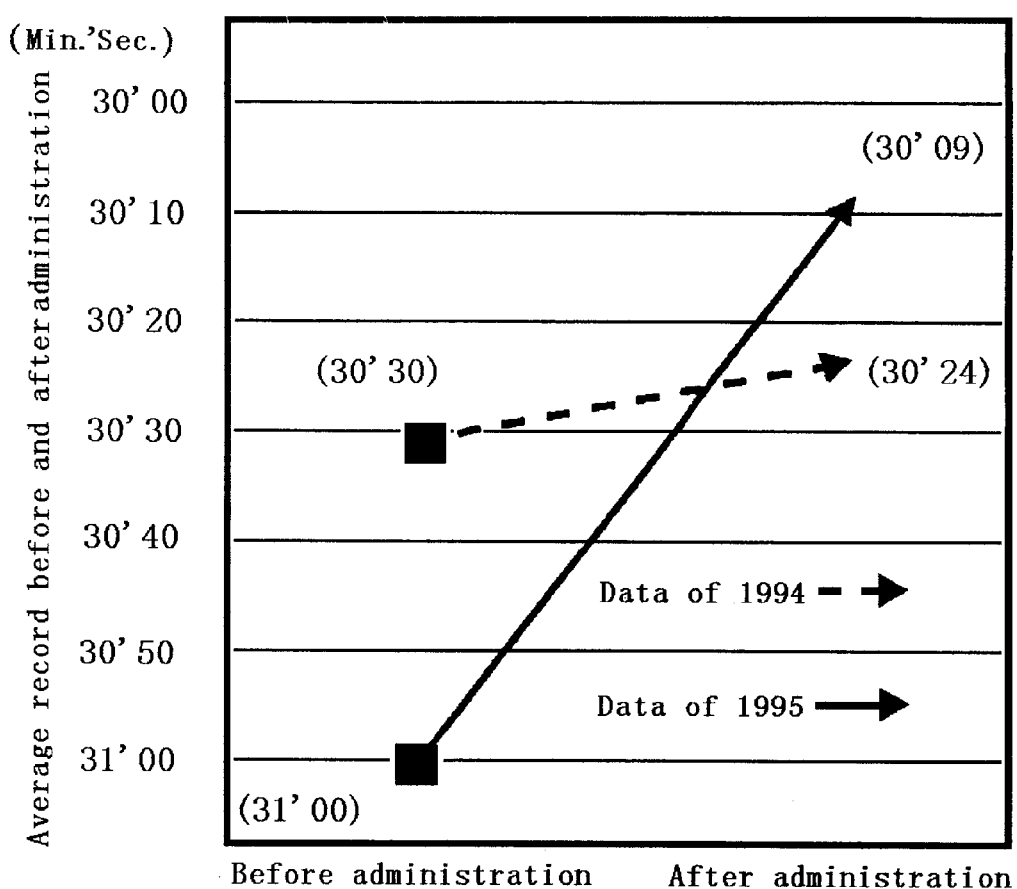
FIG. 1 illustrates the change of the team record in 10,000 m running after intake of an n-3 fatty acid for two years from the record before intake (at the same time of the year in 1994 and in 1995).

The changes of 10,000 m running records of athletes of the field and track athlete club of Juntendo University in the two years are shown in Tables 2 and 3. The 10,000 m running time in 1995 was shortened after administration of n-3 fatty acid by 51.0 seconds on the average in the team as a whole (Table 2, FIG. 1).

The change in the average time was compared between the two years; the time was shortened by 5.4 second (±0.3%) in 1994 while the time was shortened further by 45.6 seconds, i.e. a total of 51.0 seconds (±2.8%) which was a significant change (Table 4).

Figure 2:
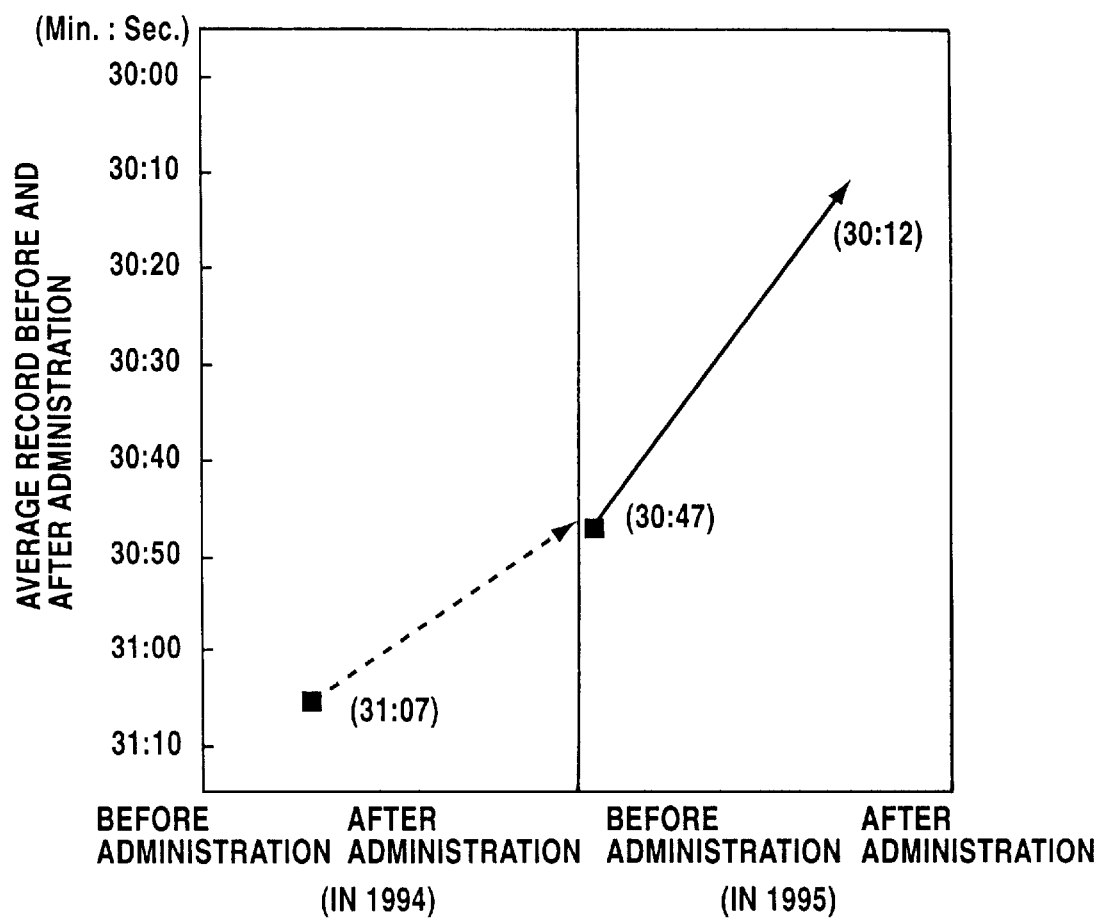
FIG. 2 illustrates the change of the average record in the same group in 10,000 m running after intake of an n-3 fatty acid for two years from the record before intake (at the same time of the year in 1994 and in 1995).
Figure 3:
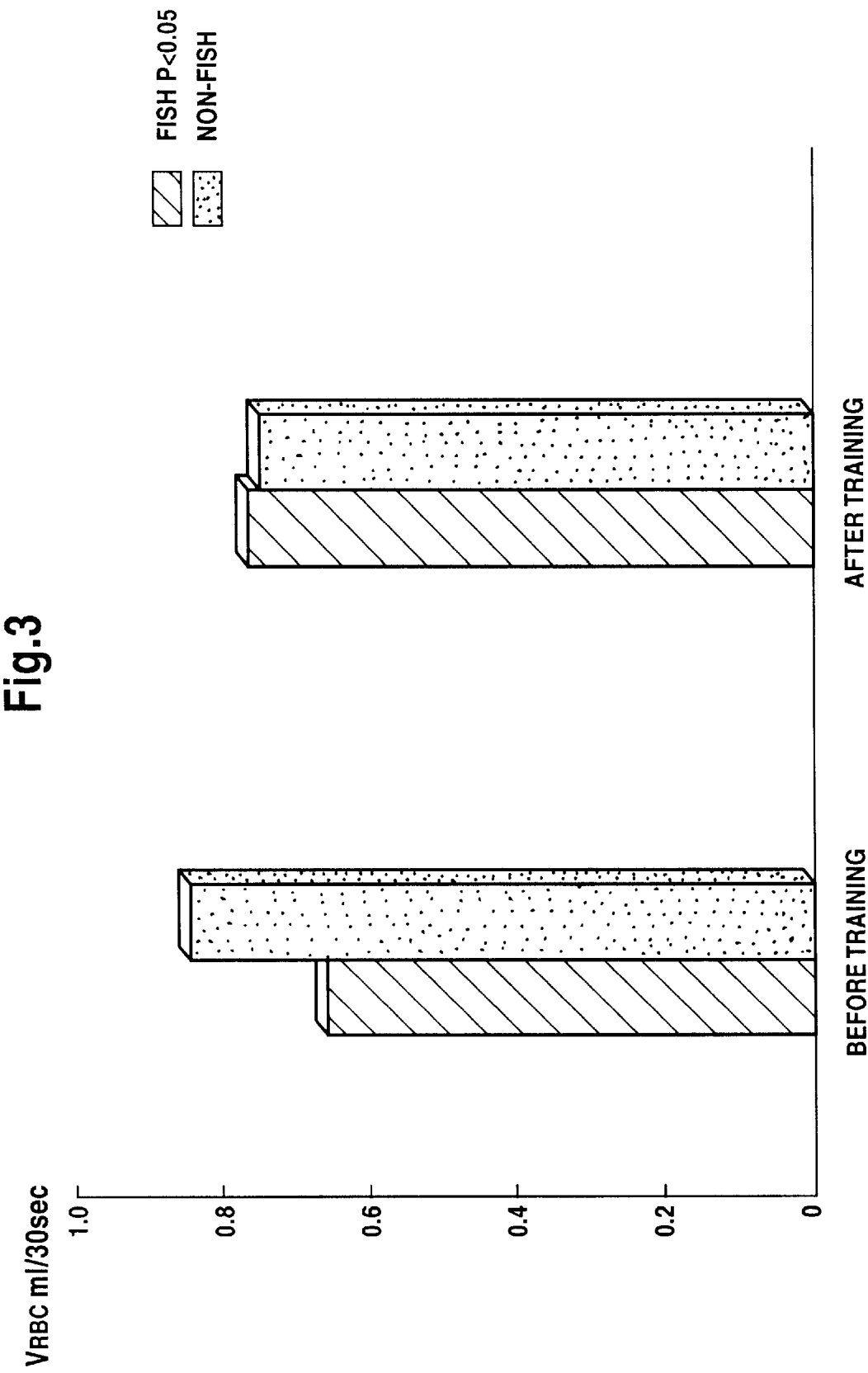
FIG. 3 illustrates the change of red blood cell fragility after 10-week administration of EPA-containing refined fish oil in healthy persons.
Figure 4:
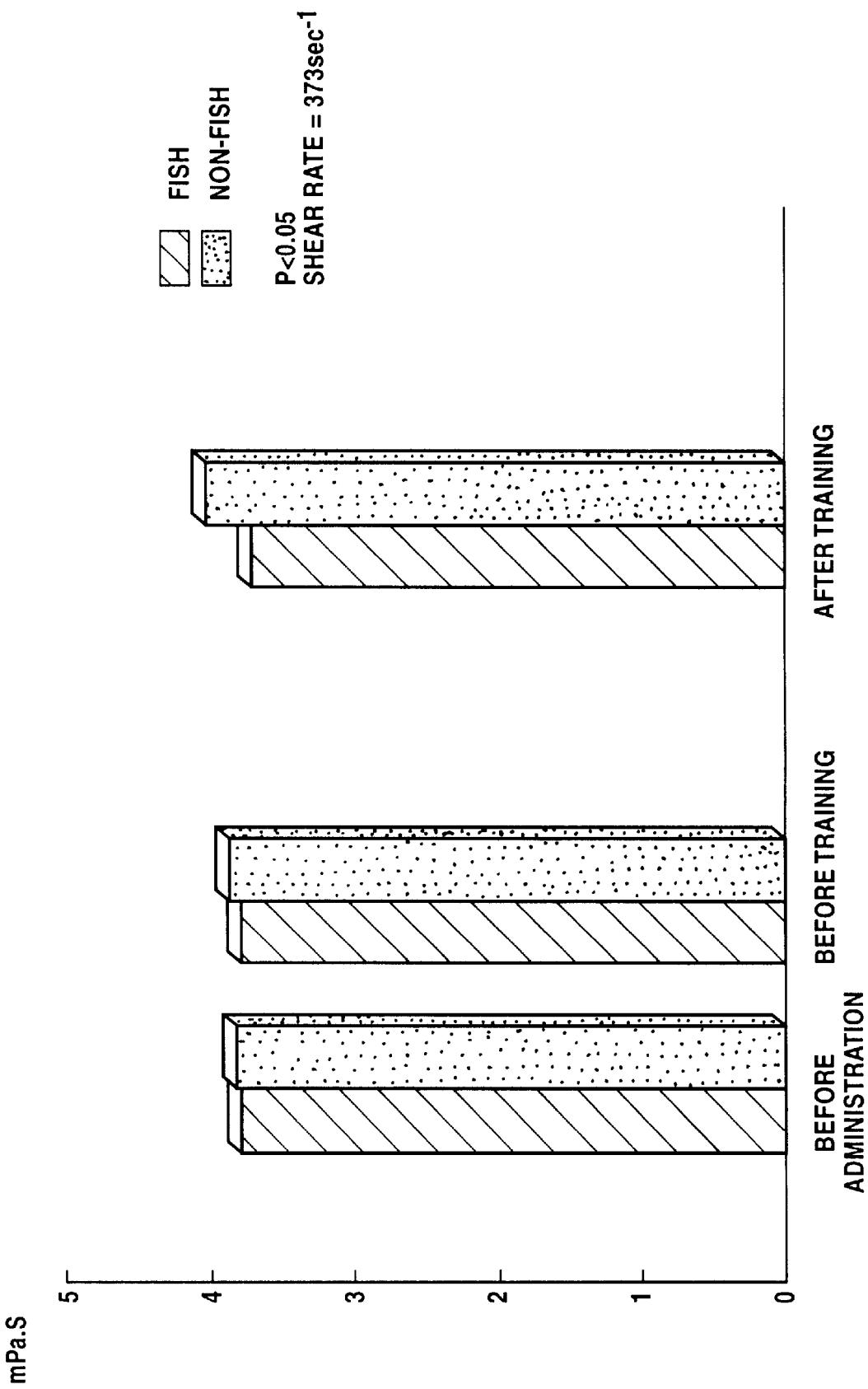
FIG. 4 illustrates the change of the yielding value [at a high shear rate of 375 $sec^{-1}$] after 10-week administration of EPA-containing refined fish oil in healthy persons.
Figure 5:
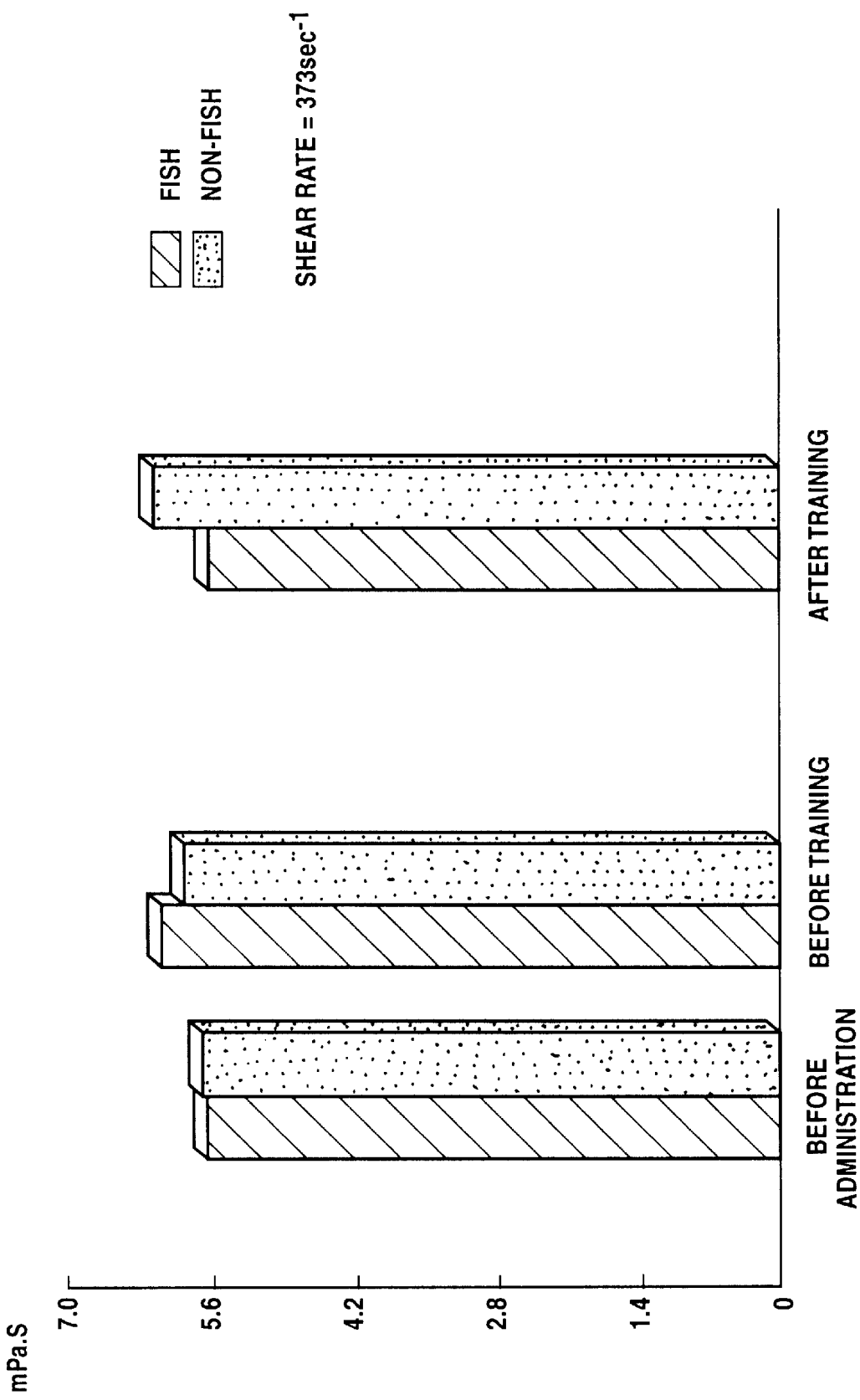
FIG. 5 illustrates the change of the yielding value [at a low shear rate of 37.5 $sec^{-1}$] after 10-week administration of EPA-containing refined fish oil in healthy persons.
Figure 6:
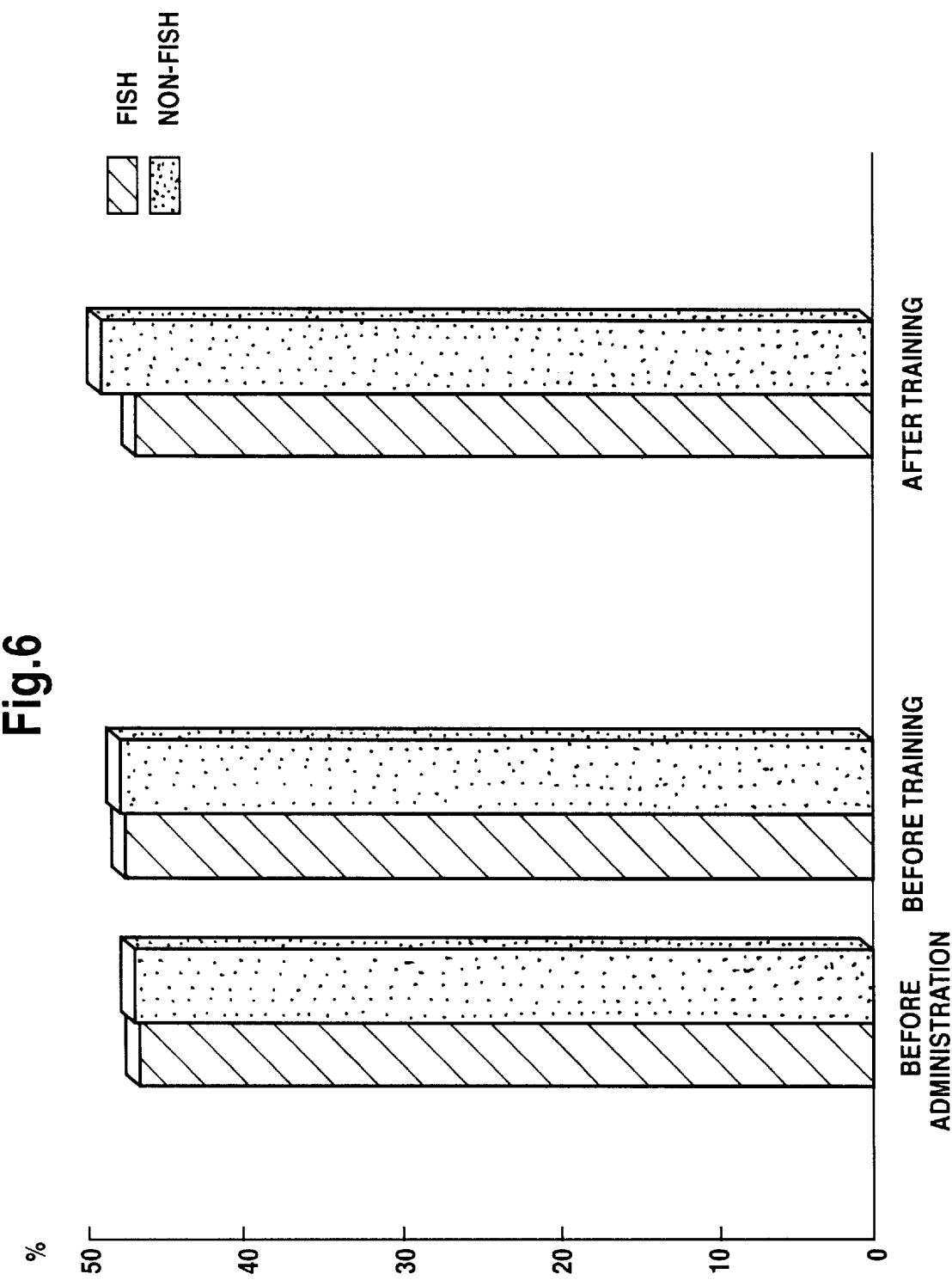
FIG. 6 illustrates the change of hematocrit after 10-week administration of EPA-containing refined fish oil in healthy persons.
Figure 7:
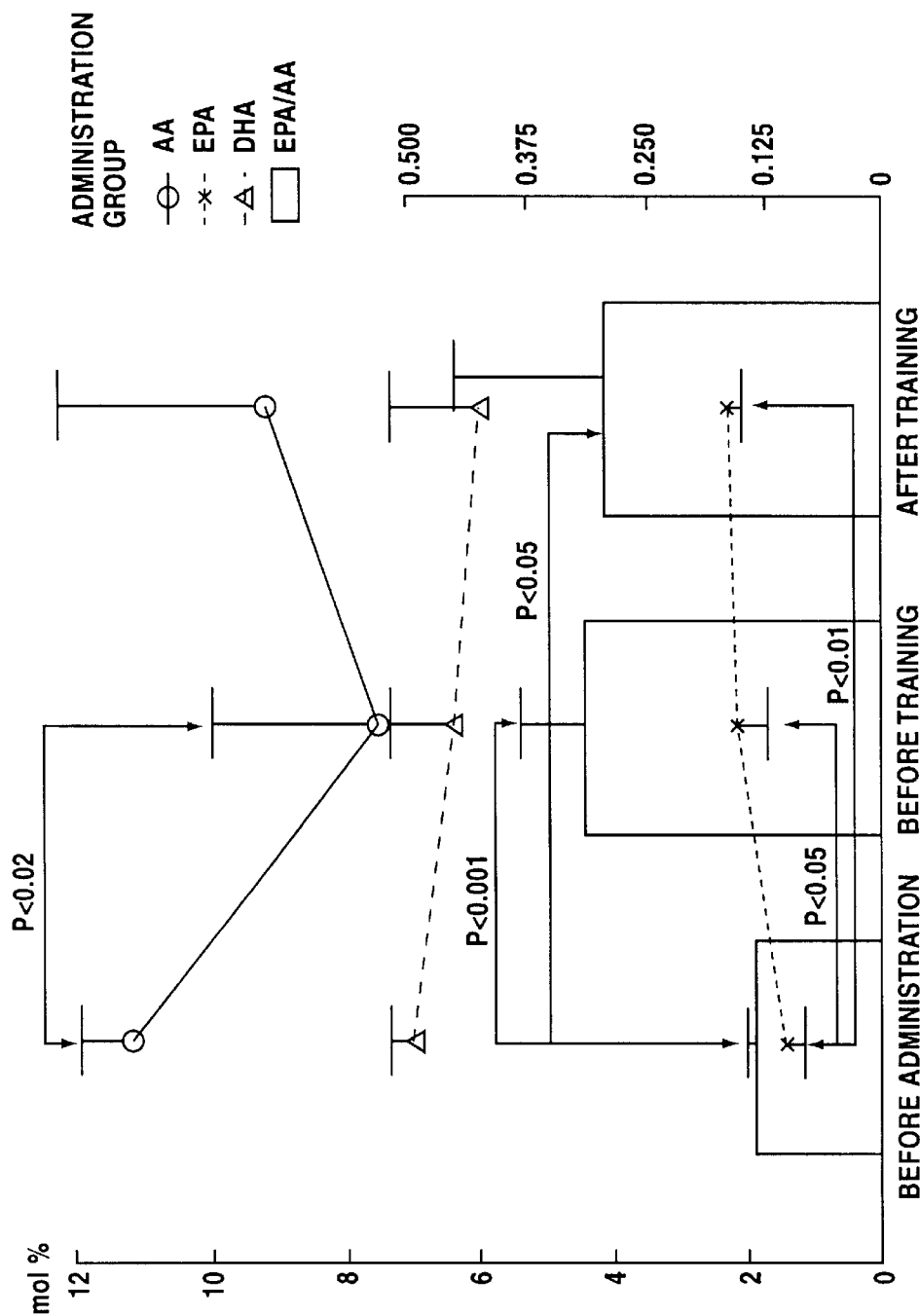
FIG. 7 illustrates the change of fatty acid composition of red blood cells in the group given fish oil.
Figure 8:
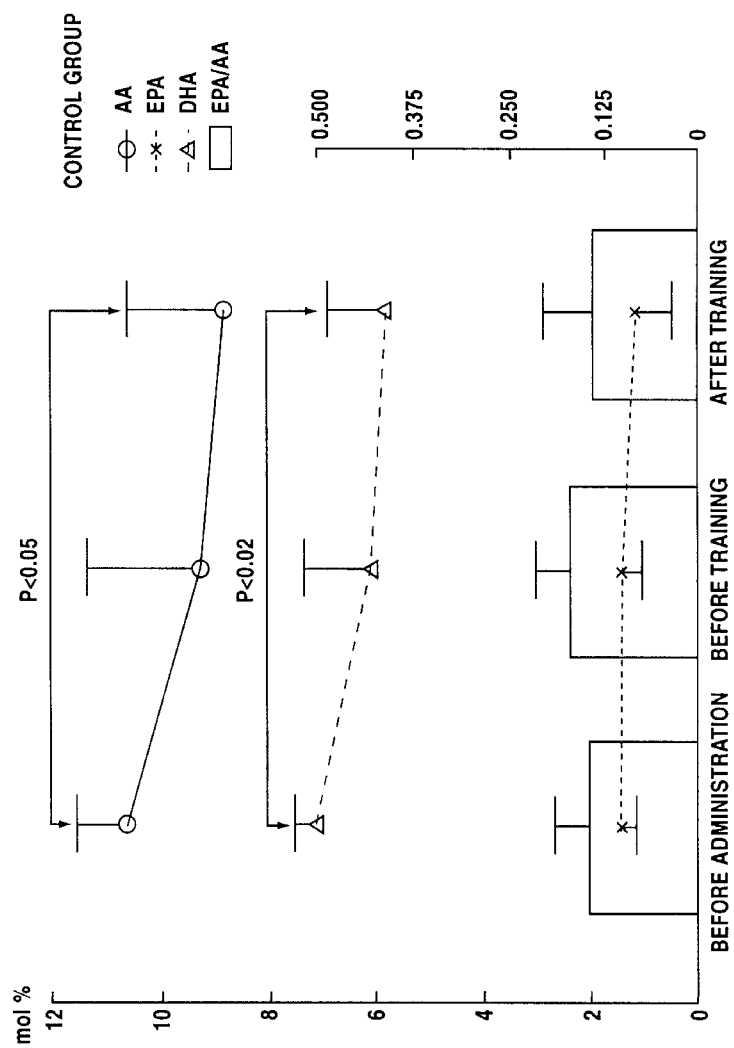
FIG. 8 illustrates the change of fatty acid composition of red blood cells in the control group.

The 10,000 m running records before and after administration of n-3 fatty acids in the same group in the two years (at the same time of the year in 1994 and in 1995) showed that the average time was shortened by 14 seconds more in 1995 than in 1994 (Table 5, FIG. 2).

On the assumption that almost the same training was performed in the two years, the supplementary administration of the n-3 fatty acid may have contributed to the shortening of the 10,000 m running time in addition to the training effect on the subjects' stamina, which suggests the efficacy of the n-3 fatty acid.

The n-3 fatty acids have been reported to be effective in increase of blood flow in the intramuscular capillaries, and in oxygen supply to the periphery resulted from improvement in fibrinolytic ability and red blood cell fragility. These effects are expected to improve various functions related to aerobic exercise capacity, and it is supposed that similar effects exerted on the subjects of this Example. This may have resulted in the remarkable difference in shortening of the 10,000 m running records between the year with n-3 fatty acid intake and the year without n-3 fatty acid intake.

It is said that the effect of training generally appears remarkably in the early stage after the start of training and is weakened with time. Similarly the record is improved more in the period when the racing level (record) is lower. From this point of view, the improvement of records noted in the present Example in the active athletes with a high racing level may be said to be a peculiar change.

These results suggest that administration of an n-3 fatty acid over a certain period may increase aerobic capacity and be effective as an auxiliary means for improving the athletic capability in long-distance running.

TABLE 2

| Name | Class | Before administration | After administration | Increment record | Difference |
|---|---|---|---|---|---|
| K. I | 4 | 30' 35" 57 | 29' 54" 25 | +2.3% | −41" 3 |
| T. Y | 4 | 30' 36" 0 | 31' 03" 01 | −2.5% | +27" 0 |
| K. H | 3 | 30' 33" 1 | 29' 27" 0 | +3.7% | −1' 06" 1 |
| S. K | 3 | 30' 40" 8 | 29' 33" 7 | +3.8% | −1' 07" 1 |
| K. S | 3 | 31' 27" 5 | 30' 00" 3 | +4.8% | −1' 27" 2 |

TABLE 2-continued

| Name | Class | Before administration | After administration | Increment record | Difference | |
|---|---|---|---|---|---|---|
| T. U | 3 | 30' 50" 5 | 30' 19" 6 | +1.7% | −30" 9 | |
| Y. I | 3 | 31' 19" 1 | 30' 46" 5 | +1.8% | −32" 6 | |
| K. O | 2 | 31' 21" 5 | 30' 42" 8 | +2.1% | −38" 7 | |
| N. M | 1 | 28' 15" 69 | 29' 11" 72 | +0.2% | −4" 0 | |
| M. M | 1 | 31' 02" 0 | 29' 50" 0 | +4.0% | −1' 12" 0 | |
| K. M | 1 | 32' 12" 7 | 29' 30" 3 | +9.2% | −2' 42" 4 | |
| M. M | 1 | 30' 57" 30 | 29' 48" 40 | +3.8% | −68" 9 | |
| S. O | 1 | 31' 26" 8 | 30' 45" 7 | +2.2% | −41" 1 | |
| T. O | 1 | 31' 49" 2 | 31' 19" 2 | +1.6% | −30" 0 | |
| Overall average | | 31' 00" 55 | 30' 09" 47 | +2.8% | −51" 0 | |
| (standard deviation) | | (40" 75) | (38" 47) | | (42" 09) | **p < 0.01 significant difference |
| students in advanced classes (sophomore, junior, senior students) | | 30' 55" 51 | 30' 13" 31 | +2.3% | −42" 20 | |
| (standard deviation) | | (21" 72) | (32" 95) | | (32" 08) | *p < 0.05 significant difference |

(The symbols − (minus) and + (plus) in the column of Difference represent improvement and reduction of record, respectively.)

TABLE 3

| Name | Class | At the same time as before administration | At the same time as after administration | Improvement of record | Difference |
|---|---|---|---|---|---|
| K. T | 4 | 29' 04" 47 | 29' 28" 94 | −1.4% | +24" 5 |
| K. I | 4 | 29' 36" 8 | 30' 04" 7 | −1.4% | +24" 9 |
| Y. N | 4 | 30' 02" 5 | 30' 37" 63 | −1.9% | +35" 1 |
| Y. S | 4 | 30' 24" 3 | 30' 46" 15 | −1.2% | +21" 9 |
| W. I | 4 | 31' 12" 0 | 30' 44" 0 | +1.5% | −28" 0 |
| J. Y | 3 | 30' 07" 7 | 29' 18" 6 | +2.8% | −49" 1 |
| T. Y | 3 | 32' 20" 7 | 31' 10" 2 | +3.8% | −1' 10" 5 |
| K. H | 2 | 30' 27" 4 | 29' 21" 2 | +3.8% | −1' 06" 2 |
| S. K | 2 | 30' 32" 96 | 30' 46" 1 | −0.7% | +13" 2 |
| I. Y | 2 | 31' 10" 3 | 31' 50" 9 | −2.1% | −40" 6 |
| Average | | 30' 30" 21 | 30' 24" 84 | +0.3% | 5" 4 |
| (standard deviation) | | (51" 74) | (47" 82) | | (41" 24) not significant |

TABLE 4

| | 1994 | 1995 | |
|---|---|---|---|
| Overall average of shortened time (standard deviation) | N = 10 −5" 4 (41" 24) | N = 14 −51" 0* (42" 09) | significantly different at 5% level |

*p < 0.05

TABLE 5

| | | | 1995 | |
|---|---|---|---|---|
| Year | 1994 | | Before administration | After administration |
| Timing | Before | After | | |
| Average record | 31' 07" 84 | 30' 47" 10 | 30' 47" 25 | 30' 12" 57 |
| Shortened time | −20" 74 | | −34" 67 | |
| (standard deviation) | (−48" 61) | | (38" 27) | |

(Note: Before and After for 1994 represent the same time as Before administration and After administration of n − 3, respectively.)

REFERENCE EXAMPLE 1

<<Effect on Hemorheology Under Normal Conditions>>
Influence of Eicosapentaenoic Acid (EPA $C_{20:5}$, n-3) on Red Blood Cell Fragility <<Summary>>

Administration of EPA.EE at 3.6 g/day for 4 weeks shifted significantly the value at the start of hemolysis, the value at the maximum hemolysis, and the value at the end of hemolysis toward the lower osmotic pressure side, suggesting that the red blood cell membrane was strengthened. It is meaningful that increased red blood cell fragility and strengthened membrane were found at the same time as in this study; thus not only the safety of administration was demonstrated but also it was supposed that vascular wall cells and somatic cells became more flexible and safer.

<<Purpose>>

There are various factors that affect blood viscosity, including red blood cell fragility, hematocrit, and plasma viscosity, which are considered to interact mutually to change the viscosity. EPA is supposed to improve red blood cell fragility among these factors. Red blood cell fragility is dependent on the surface area/cubic volume ratio of red blood cells, internal viscosity of red blood cells, viscoelasticity of the membrane, etc. Efficacy of EPA is supposed to consist in its effect on the fluidity of the membrane; EPA is able to make blood flow smoothly, particularly by making red blood cells fragile so that they can take the form suitable for passing through the capillaries smoothly.

On the other hand it was reported for several diseases that there is a relationship between decrease of red blood cell fragility and hardening of red blood cell membrane, suggesting that increased fluidity of the red blood cell membrane may weaken red blood cells.

Then in this study, EPA.EE was administered to healthy persons for 4 weeks, and the effect of EPA on red blood cell fragility was investigated with the coil planet centrifuge method. This method was developed by Kimura et al. for measurement of red blood cell membrane osmotic resistance.

<<Method>>

Purified EPA.EE obtained from the edible part of sardine was administered to 10 healthy persons (mean age: 36 years) at 3.6 g per day for 4 weeks.

The test was performed according to the method of Reid's et al. That is, the time required for 0.5 ml of blood to pass through the 5 $\mu$m nucleopore membrane filter under the water pressure corresponding to the water column of 30 cm was measured, the time was converted into the volume of cells that passed in 30 seconds by using the hematocrit value ($V_{RBC}$ml/30 sec), and the volume was used as the index of red blood cell fragility.

For statistical analysis the Student's t-test (paired) was used with the significance level of two-sided 5%.

<<Results>>

Administration of EPA.EE to 10 healthy persons at 3.6 g daily for 4 weeks increased the EPA content in the red cell membrane from 2.01±0.35 mol % to 4.00±0.34 mol %. The result of measurement of blood rheologic parameters is shown in Table 6.

The yield value of blood viscosity (at a low shear rate= 37.5 $sec^{-1}$) was decreased significantly (p<0.01), and also the yield value (at a high shear rate=375 $sec^{-1}$) was decreased significantly (p<0.001). Red blood cell fragility was increased significantly (p<0.05) and plasma viscosity was decreased significantly (p<0.05).

Figure 9:
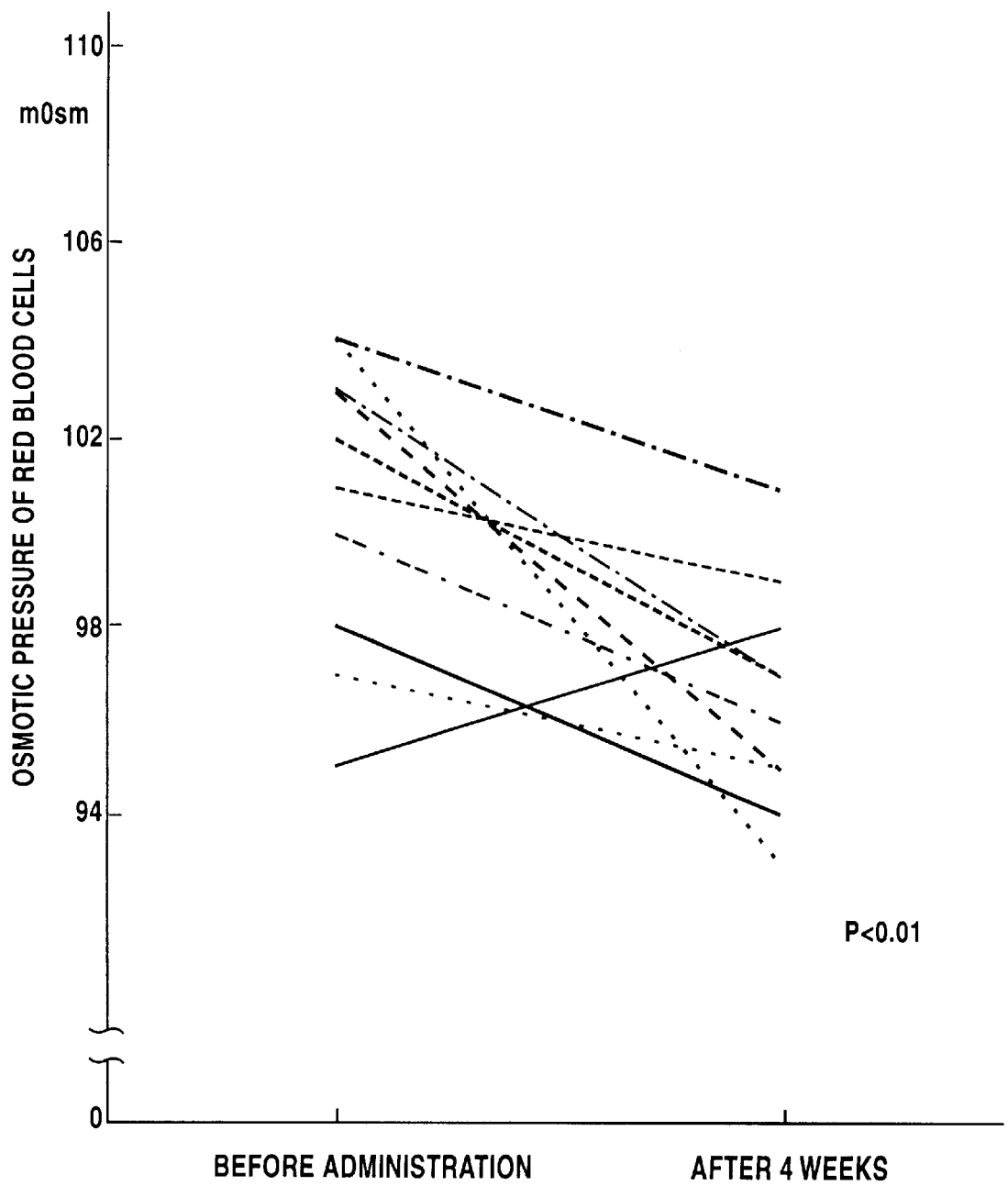
FIG. 9 illustrates the influence of 4-week administration of EPA-EE on red blood cell osmotic pressure (at the start of hemolysis) in healthy persons. The axis of ordinates represents the osmotic pressure of red blood cells.
Figure 10:
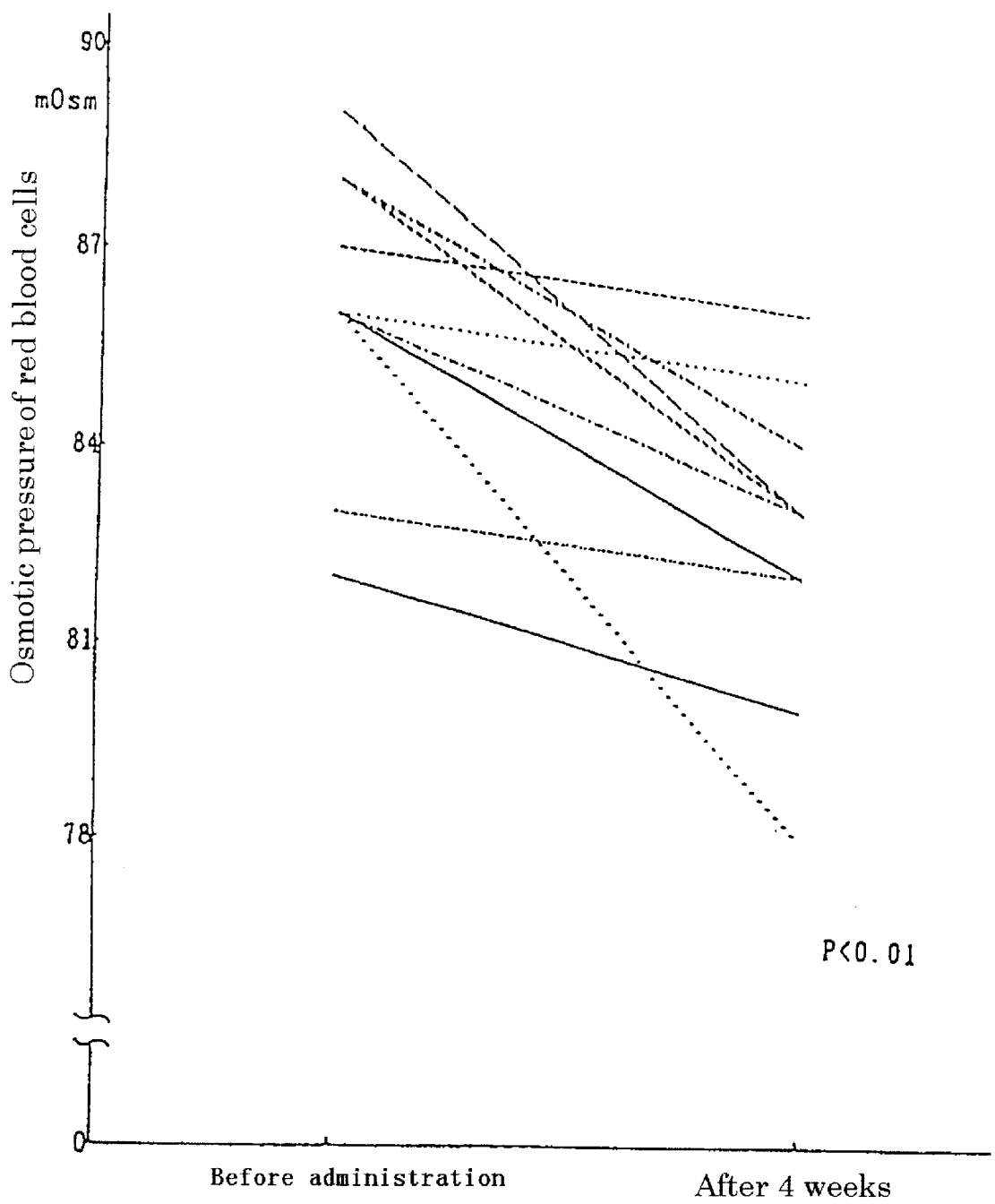
FIG. 10 illustrates the influence of 4-week administration of EPA-EE on red blood cell osmotic pressure (at the maximum hemolysis) in healthy persons.

The results of measurement of red blood cell membrane osmotic resistance (A) (B) and (C) are shown in FIGS. 9 to 11.

(A) Osmotic pressure of red blood cells at the start of hemolysis was decreased from the value before administration (100.7±3.13 mOsm) to the value after administration (96.5±2.42 mOsm), (B) osmotic pressure of red blood cells at the time of maximum hemolysis was decreased from the value before administration (86.1±2.18 mOsm) to the value after administration (82.6±2.32 mOsm), and (C) osmotic pressure of red blood cells at the end of hemolysis was decreased from the value before administration (66.0±3.33 mOsm) to the value after administration (69.4±2.76 mOsm) significantly (p<0.01).

TABLE 6

|  | Before administration | After 4-week administration | Test |
| --- | --- | --- | --- |
| Whole blood viscosity Yield value = 37.5 sec – 1 | 5.93 ± 0.815 | 5.57 ± 0.704 | P < 0.01 |
| Yield value = 375 sec – 1 | 3.96 ± 0.458 | 3.75 ± 0.445 | P < 0.001 |
| Plasma viscosity | 1.33 ± 0.050 | 1.30 ± 0.055 | P < 0.05 |
| Red blood cell fragility | 0.681 ± 0.1062 | 0.768 ± 0.1253 | P < 0.05 |
| Hematocrit | 46.1 ± 3.45 | 45.1 ± 2.85 | N.S. |

<<Discussion>>

In this study, the EPA content in red blood cells was almost doubled from 2.01±0.35 mol % to 4.00±0.34 mol %, and significant decrease of blood viscosity and significant increase of red blood cell fragility were also noted.

The lipid in the red blood cell membrane is composed of free cholesterol (FC), phosphatidyl ethanolamine (PE), phosphatidyl serine (PS), phosphatidyl choline (PC), and sphingomyelin (SM). PE and PS are abundant in the inner layer of the double layer of lipid, while PC and SM are present predominantly in the outer layer and FC is distributed uniformly both in the outer layer and in the inner layer. Among these PC contributes to the fluidity of the membrane while FC and SM make the membrane viscous to stiffen the membrane. SM is said to be more powerful than FC in stiffening the membrane. According to the report of Tamura et al. who administered EPA.EE at 3.6 g/day and measured the content of arachidonic acid (AA) and the content of EPA in phospholipid fractions of platelets, the AA content in PC and PE decreased significantly and the EPA content increased in PC, PE, PI, and PS. The same may be true for red blood cells. Among these findings, decrease of AA and increase of EPA in PC which is effective in increasing of fluidity of the membrane are especially interesting. The fact that EPA having the lowest viscosity among fatty acids is increased particularly in PC in the membrane suggests that the EPA content may contribute to fluidity of the membrane, which may weaken the membrane. In this study administration of EPA.EE at 3.6 g/day for 4 weeks shifted the values at the start of hemolysis, at the time of maximum hemolysis, and at the end of hemolysis toward the lower osmotic pressure side, suggesting that the membrane of red blood cells was strengthened.

It is meaningful that increased red blood cell fragility and strengthened membrane were found at the same time in this study; thus not only the safety of administration was demonstrated but also it was found that vascular wall cells and somatic cells became more flexible and safer.

EXAMPLE 2

<<Effect on the Change in Blood Rheology During Exercise>>

1. Dosage and Preparations Used
1) Administration at 1.6 g/day on EPA basis is aimed.
2) Refined fish oil capsules 300 mg containing 28% of EPA and 12% of DHA are administered at 18 capsules/day, i.e. 9 capsules each after breakfast and after supper.
2. Number of Subjects
1) Two groups including 6 subjects each [EPA group (fish), non-EPA group (non-fish)]
3. Method
1) According to the schedule shown in Table 7, refined fish oil capsules are administered to the EPA group at 18 capsules/day from 10 weeks before the start of training in the highland till the end of the training.
2) For both groups, the items described in the following section were examined at the start of administration, at the start of training in the highland, and at the end of the training.

TABLE 7

| Start month | 2 months of training in highland | 4.5 months after end of training in highland |
|---|---|---|
| Start of adminstration | | end of adminstration |
| |— 10 weeks —| | |
| 1st | 2nd | 3rd |
| blood sampling measurement of excercise capacity | blood sampling measurement of excercise capacity | blood sampling measurement of excercise capacity |

4. Examination items
1) Biochemical examination items

Items (a) Fatty acid composition (plasma, red blood cell membrane phospholipid)

(b) Red blood cell fragility (c) Yield value (d) Amino acid composition

2) Physiological examination items (exercise capacity)

(1) Items (a) Maximum oxygen intake (b) Measurement in MSS (maximal steady state): Change and improvement of stamina in the EPA group and in the non-EPA group.

Blood was drawn at rest before and after each training, and examined for the items described above. The concentration of lactic acid in blood was determined after running at two different speed before and after each training, and the running speed corresponding to 4 mmol/l was calculated (MSS). Improvement of stamina was estimated by using this MSS value as the index.

<<Results>>

As shown in FIGS. 3 to 8 and Tables 8 and 9, hematocrit is not different between the fish oil group and the non-fish oil group, though red blood cell fragility was increased significantly in the fish oil group and increase of whole blood viscosity noted in the non-fish oil group was not noted in the fish oil group.

TABLE 8

| | Fish oil group | | | Non-fish oil group | | |
|---|---|---|---|---|---|---|
| | Before administration | After administration | Test | Before administration | After administration | Test |
| RBC | 491.67 (8.36) | 498.00 (19.38) | n.s. | 488.00 (20.21) | 502.00 (23.36) | $p < 0.05$ |
| Hemoglobin g/dl | 15.00 (0.39) | 15.02 (0.44) | n.s. | 15.25 (0.44) | 15.33 (0.51) | n.s. |
| MCV fl | 91.17 (2.33) | 89.90 (1.85) | $p < 0.05$ | 94.67 (3.54) | 92.62 (3.57) | $p < 0.001$ |
| MCH pg | 30.52 (0.63) | 30.17 (0.78) | n.s. | 31.28 (0.81) | 30.57 (1.06) | $p < 0.01$ |
| MCHC % | 33.47 (0.56) | 33.57 (0.42) | n.s. | 33.05 (0.54) | 33.02 (0.25) | n.s. |
| Serum Fe µg/dl | 116.67 (30.30) | 153.83 (36.10) | $p < 0.05$ | 103.17 (22.18) | 129.00 (14.32) | $p < 0.05$ |

TABLE 9

| | Group | AW5 | AW50 | Ht | Casson |
|---|---|---|---|---|---|
| Start | Group A (EPA administration) | 5.67 ± 0.530 | 3.80 ± 0.309 | 46.6 ± 2.30 | 0.162 ± 0.0528 X-X |
| | Group B (Control) | 5.73 ± 0.245 | 3.84 ± 0.194 | 47.1 ± 1.08 | 0.156 ± 0.0366 |
| Before training | Group A (EPA administration) | 6.08 ± 0.321 X | 3.82 ± 0.172 | 47.5 ± 1.23 | X 0.238 ± 0.545 |
| | Group B (Control) | 5.87 ± 0.540 | 3.90 ± 0.226 | 47.7 ± 1.17 | 0.181 ± 0.0512 |
| After training | Group A (EPA administration) | X 5.63 ± 0.478 | 3.79 ± 0.250 X | 47.0 ± 1.27 X | 0.162 ± 0.0637 |
| | Group B (Control) | 6.15 ± 0.484 | 4.05 ± 0.191 | 49.2 ± 2.32 | 0.230 ± 0.1464 |

X p < 0.1
X-X p < 0.05

INDUSTRIAL APPLICABILITY

It is possible to provide a health food for preventing risks such as sudden death during exercise and a composition having a capability of removing risk factors during exercise which are applicable to the field of preventive drugs. It is possible to provide a composition having a capability of removing risk factors during exercise for healthy persons such as sports professionals, sports players or athletes, sports enthusiasts, persons who want to do sports, and persons who aim to improve stamina.

It is possible to provide foods for improving exercise capacity for healthy persons (sports enthusiasts, persons who want to do sports, persons who aim to improve stamina, etc.). It is possible to provide nutritious foods for improving exercise capacity which are effective as auxiliary means for enhancing aerobic capacity of sports players or athletes and improving exercise capacity of long-distance running.

What is claimed is:

1. A method of removing risk factors during exercise of a person comprising administering to that person a composition containing an n-3 highly unsaturated fatty acid or a derivative thereof as an active ingredient.

2. The method of claim 1, wherein said n-3 highly unsaturated fatty acid is eicosapentaenoic acid and/or docosahexaenoic acid.

3. The method of claim 1, wherein said n-3 highly unsaturated fatty acid is in the form of natural triglyceride.

4. The method of claim 2, wherein said n-3 highly unsaturated fatty acid is in the form of natural triglyceride.

5. The method of claim 3, wherein said n-3 highly unsaturated fatty acid is fish oil.

6. The method of claim 4, wherein said n-3 highly unsaturated fatty acid is fish oil.

7. A method of preventing athletic anemia of a person comprising administering to that person a composition containing an n-3 highly unsaturated fatty acid and/or a derivative thereof as an active ingredient.

8. The method of claim 7, wherein said n-3 highly unsaturated fatty acid is eicosapentaenoic acid and/or docosahexaenoic acid.

9. The method of claim 7, wherein said n-3 highly unsaturated fatty acid is in the form of natural triglyceride.

10. The method of claim 8, wherein said n-3 highly unsaturated fatty acid is in the form of natural triglyceride.

11. The method of claim 9, wherein said n-3 highly unsaturated fatty acid is fish oil.

12. The method of claim 10, wherein said n-3 highly unsaturated fatty acid is fish oil.

13. The method of any one of claims 1 to 12, wherein said composition is a food.

14. A method of removing risk factors during exercise of a person comprising administering to that person a pharmaceutical composition comprising an n-3 highly unsaturated fatty acid and/or a derivative thereof as a pharmaceutically active ingredient.

15. The method of claim 14, wherein said n-3 highly unsaturated fatty acid is eicosapentaenoic acid and/or docosahexaenoic acid.

16. The method of claim 14, wherein said n-3 highly unsaturated fatty acid is in the form of natural triglyceride.

17. The method of claim 15, wherein said n-3 highly unsaturated fatty acid is in the form of natural triglyceride.

18. The method of claim 16, wherein said n-3 highly unsaturated fatty acid is fish oil.

19. The method of claim 17, wherein said n-3 highly unsaturated fatty acid is fish oil.

20. The method of any one of claims 14 to 19, wherein said derivative of n-3 highly unsaturated fatty acid is a pharmaceutically acceptable salt, ester or amide.

21. The method of claim 1, wherein the maximum oxygen intake and the anaerobic threshold value are enhanced by at least 3%.

22. The method of claim 21, wherein said n-3 highly unsaturated fatty acid is eicosapentaenoic acid and/or docosahexaenoic acid.

23. The method of claim 22, wherein said composition is liquid or solid.

24. The method of claim 23, wherein said composition is included in capsules.

25. A method of improving exercise capacity of a person comprising administering to that person a composition containing an n-3 highly unsaturated fatty acid or a derivative thereof as an active ingredient.

26. The method of claim 25, wherein the maximum oxygen intake and the anaerobic threshold value are enhanced by at least 3%.

27. The method of claim 25, wherein said n-3 highly unsaturated fatty acid is eicosapentaenoic acid and/or docosahexaenoic acid.

28. The method of claim 27, wherein said composition is liquid or solid.

29. The method of claim 28, wherein said composition is included in capsules.

* * * * *